(12) United States Patent
Van der Heide et al.

(10) Patent No.: US 6,978,690 B1
(45) Date of Patent: Dec. 27, 2005

(54) APPARATUS FOR THE INTERNAL INSPECTION OF PIPES AND TUBES AND THE LIKE

(75) Inventors: Siemen Roelof Van der Heide, Nijmegen (NL); Leonardus Johannes Gruitroij, Westervoort (NL); Joost Martinus Hermanus Parent, Ville d'Anjou (CA); Christiaan Willem Schomper, Ede (NL)

(73) Assignee: A. Hak Industrial Services B.V., Rhenen (NL)

(*) Notice: Subject to any disclaimer, the term of this patent is extended or adjusted under 35 U.S.C. 154(b) by 0 days.

(21) Appl. No.: 09/936,632

(22) PCT Filed: Mar. 10, 2000

(86) PCT No.: PCT/NL00/00163

§ 371 (c)(1),
(2), (4) Date: Feb. 21, 2002

(87) PCT Pub. No.: WO00/54043

PCT Pub. Date: Sep. 14, 2000

(30) Foreign Application Priority Data

Mar. 11, 1999 (NL) .............................. NL 1011525

(51) Int. Cl.⁷ ............................................. G01G 9/00
(52) U.S. Cl. .................... 73/865; 73/623; 73/624; 73/866.5; 73/865.9; 73/865.8; 73/625

(58) Field of Search .......................... 73/623, 622, 601, 73/432.1, 865.9, 865.8, 866.5, 865, 624, 73/865.5, 625; 15/104

(56) References Cited

U.S. PATENT DOCUMENTS

| | | | | |
|---|---|---|---|---|
| 4,560,931 A | * | 12/1985 | Murakami et al. ............ | 73/623 |
| 4,679,448 A | * | 7/1987 | Lund ......................... | 73/866.5 |
| 5,398,560 A | * | 3/1995 | Zollingger et al. ........... | 73/623 |
| 5,454,267 A | | 10/1995 | Moreau et al. | |
| 5,565,633 A | * | 10/1996 | Wernicke .................... | 73/623 |
| 5,640,780 A | * | 6/1997 | Kermabon ................... | 33/544 |
| 5,770,800 A | * | 6/1998 | Jenkins et al. ............... | 73/623 |
| 6,318,194 B1 | * | 11/2001 | Marvin et al. ............ | 73/865.8 |

FOREIGN PATENT DOCUMENTS

| EP | 58129255 | 8/1983 |
|---|---|---|
| EP | 6100756 | 1/1986 |

* cited by examiner

Primary Examiner—Hezron Williams
Assistant Examiner—André K. Jackson
(74) Attorney, Agent, or Firm—Peacock Myers, P.C.; Jeffrey D. Myers

(57) ABSTRACT

An apparatus for the internal inspection of pipes and tubes or the like, comprising an ultrasonic measuring head and a cable coupled to the measuring head, which cable can be coupled outside the pipe or tube to be measured to a device processing the measuring data, the apparatus being provided at its distal end but behind the measuring head, with a reel for winding the cable on and off.

18 Claims, 1 Drawing Sheet

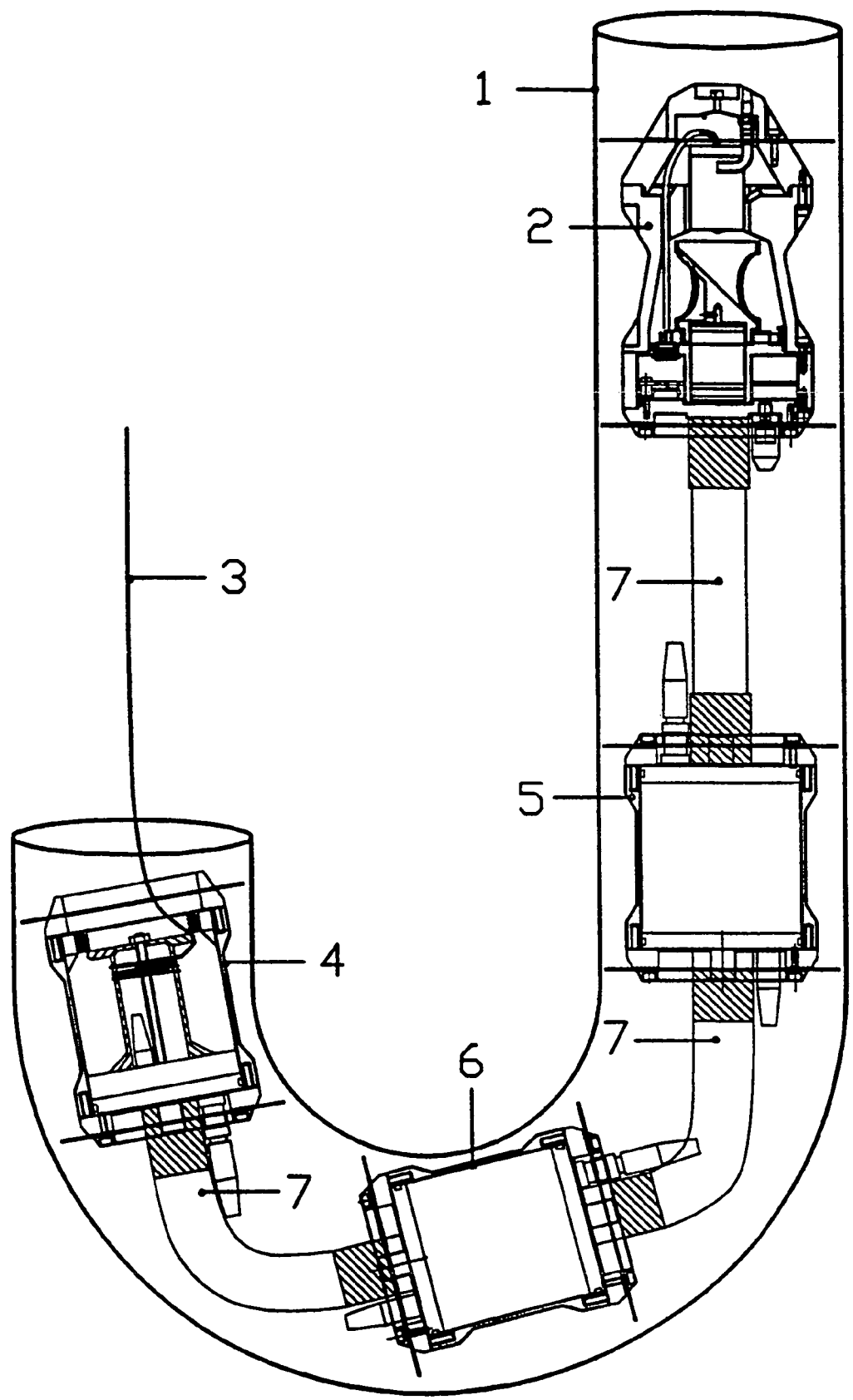

APPARATUS FOR THE INTERNAL INSPECTION OF PIPES AND TUBES AND THE LIKE

CROSS-REFERENCE TO RELATED APPLICATIONS

This application is a national entry application of International Patent Application Serial No. PCT/NL00/00163, entitled "Apparatus for the Internal Inspection of Pipes and Tubes and the Like" to Siemen Roelof Van der Heide, et al., having an international filing date of Mar. 10, 2000, and claiming priority to Netherlands Patent Application Serial No. 1011525, having a filing date of Mar. 11, 1999, and the specifications thereof are incorporated herein by reference.

BACKGROUND OF THE INVENTION

1. Field of the Invention

The invention relates to an apparatus for the internal inspection of pipes and tubes or the like, comprising an ultrasonic measuring head and a cable coupled to the measuring head, which cable can be coupled outside the pipe or tube to be measured to a device processing the measuring data. Such an apparatus is used for the internal inspection of pipes and tubes of in particular industrial furnaces in the petrochemical and chemical industry or in other (heavy) industries. The inspection serves for the detection of internal and surface corrosion such as pitting, but also for the detection of a reduction in wall thickness, mechanical deformations such as dents, and ovalities resulting from local overheating. In addition, the apparatus can be used to determine to what extent the pipes and tubes are fouled. To perform the measurement with the apparatus according to the preamble of claim 1, it is advantageous to use a measuring head as patented and specified in applicant's Dutch patent 1006007.

2. Description of Related Art

One of the problems that manifests itself when inspecting industrial furnaces of the above kind, is that they are constructed from a large number of horizontal or vertical pipes that are coupled by means of so-called return bends. These return bends have a radius of 1D, that is to say a bend diameter that is equal to the internal diameter of the pipe, and a gradient of 180°. As a result, every known apparatus for the internal inspection of such pipes and tubes will become lodged after two and at the most after three bends. A foremost problem is, however, that there is no known system of dimensions that allow the passage through bends having a radius of 1D.

BRIEF SUMMARY OF THE INVENTION

It is the object of the invention to make this possible and to provide an apparatus that can be used irrespective of the number of bends to be taken in the furnace to be inspected, and which in addition is designed such that it is possible to pass through bends having a radius of 1D.

DETAILED DESCRIPTION OF THE INVENTION

In a first aspect the invention is therefore characterized in that at its distal end but behind the measuring head, the apparatus is provided with a reel for winding the cable on and off.

The fact that in the apparatus according to the invention the cable reel is located in the furnace and not as in the known system outside the furnace, makes it possible to pass through any number of bends without the apparatus becoming lodged in the pipes or tubes to be inspected.

Various kinds of cables may be used. For example, a cable may be used by which simultaneously a voltage is supplied to the measuring head in the furnace.

In a preferred embodiment of the apparatus according to the invention the same is characterized in that the cable is a glass-fibre cable and in that the apparatus near its distal end is provided with a feed device for feeding the measuring head. By using a glass-fibre cable, the cable can be very thin and may, for example, have a thickness of less than 0.125 mm, and longer cables may be wound onto the reel, for example, up to a length of 3 km, allowing very complex furnaces of extensive length to be inspected.

In a further aspect of the invention the apparatus is characterized in that the measuring head, the reel, the feed device, and any possible electronics present near the distal end are each incorporated individually in carrier members that can be moved through the pipe or tube. This supports the possibility that the apparatus is suited for passing through bends having a radius of 1D, which with the prior art apparatuses is in itself already a problem when applied with such tubes. Conveniently, the individual carrier members are then sequentially interconnected by means of flexible couplings.

One preferred embodiment of the apparatus according to the invention is characterized in that the flexible couplings are formed by hydraulic tubes with a steel covering. The fact that the tubes are provided with a steel covering means that the apparatus can be subjected to a tensile strain, which strain occurs in practice when the apparatus is moved in the furnace tubes by means of a differential pressure preceding and following the sequentially interconnected carrier members.

For the smooth passage through the bends in the pipes or tubes to be inspected, the length of the hydraulic tubes is advisably chosen in accordance with the flexural stiffness of the tubes.

The invention will now be elucidated with reference to the drawing, which in a single figure schematically and in cross section shows the portion of the tube to be inspected, with the apparatus for carrying out the inspection inserted therein.

To elucidate the invention, a tube portion 1 to be inspected is shown, comprising a so-called 1D bend, that is to say a bend whose radius is equal to the diameter of the tube 1. The bend shown has a gradient of 180°, that is to say the bend is a complete U-shape. Inserted into the tube 1 is an apparatus for the inspection of the tube, comprising an ultrasonic measuring head 2 and a glass-fibre cable 3 extending outside the respective tube of the furnace to be inspected, and which is coupled in the manner known to the person skilled in the art to a data processing unit, for example, a computer, for storing and optionally further processing the measuring data.

The glass-fibre cable 3 is unwound from a reel 4 which, in the forward-moving direction of the measuring head 2, is located behind said measuring head 2 at the distal end of the apparatus. To allow the apparatus to be moved forward through the tube 1, the cable 3 can be unwound from the reel 4, and to withdraw the apparatus from the tube 1, the glass-fibre cable 3 is rewound onto the reel 4.

The apparatus further comprises an electronic control unit 5 for the measuring head 2 and a feed device 6 with battery supply for feeding the measuring head 2. As is clearly shown in the FIGURE, the measuring head 2, the reel 4, the control electronics 5, and the feed device 6 are each individually incorporated in the carrier members that are movable through the pipe or tube 1.

The individual carrier members of the measuring head 2, the reel 4, the feed device 6, and the control electronics 5 are sequentially interconnected by means of flexible couplings 7. These flexible couplings 7 are formed by hydraulic tubes with a steel covering so that the couplings 7 can also tolerate a tensile strain, while primarily providing the possibility for the apparatus to pass through bends of the tubes 1 to be inspected. The lengths of the flexible couplings 7 should be selected in accordance with the degree of flexural stiffness of the hydraulic tubes from which the flexible couplings 7 are formed.

In a practical embodiment of the apparatus according to the invention, the flexible coupling 7 is formed as an approximately 10-cm long hydraulic tube, provided at both ends with an iron coupling connected with the housing of the carrier members. In the tube, three woven steel coverings may, for example, be provided for absorbing the tensile forces that are necessary for the transportation of the apparatus in the tube 1. Said steel coverings provide the flexible coupling 7 with some rigidity. By giving the flexible coupling a suitable length, the coupling may be designed such as to still allow passage through the bends in the tube.

When using a battery supply near the measuring head as explained above, the feed supply for the measuring head 2 does not need to come from outside the furnace to be inspected. The role of the applied glass-fibre cable 3 is then only that of data transporter.

To the person skilled in the art it will be obvious that the example discussed above serves merely to elucidate the appended claims and that diverse variations are possible, all within the scope of said claims.

What is claimed is:

1. An apparatus for internal inspection of a pipe or tube, said apparatus comprising:
    a separate ultrasonic measuring head sufficiently small to pass through one or more 1D bends in the pipe or tube;
    at least one separate carrier member sufficiently small to pass through one or more 1D bends in the pipe or tube;
    a separate cable reel sufficiently small to pass through one or more 1D bends in the pipe or tube; and
    a plurality of flexible coupling tubes which sequentially interconnect said measuring head, said at least one carrier member, and said cable reel, said coupling tubes having a diameter substantially smaller than a diameter of said carrier member and having sufficient tensile rigidity to enable transportation of said apparatus in the pipe or tube; and
    wherein said coupling tubes comprise at least one steel covering.

2. The apparatus of claim 1 wherein said cable reel comprises an axis of rotation substantially parallel to a direction of travel of said apparatus.

3. The apparatus of claim 1 wherein said cable reel is operable to wind and unwind a cable.

4. The apparatus of claim 3 wherein said cable comprises a data communications cable.

5. The apparatus of claim 4 wherein said cable comprises a glass-fibre cable.

6. The apparatus of claim 5 wherein said cable comprises a thickness of less than approximately 0.125 mm.

7. The apparatus of claim 5 wherein said cable comprises a length of up to approximately 3 km.

8. The apparatus of claim 3 wherein said cable supplies power to said apparatus.

9. The apparatus of claim 1 wherein said at least one carrier member comprises a power supply.

10. The apparatus of claim 9 wherein said power supply comprises one or more batteries.

11. The apparatus of claim 1 wherein said at least one carrier member comprises an electronics.

12. The apparatus of claim 11 wherein said electronics comprise an electronic control unit.

13. The apparatus of claim 1 wherein said coupling tubes comprise hydraulic tubes.

14. The apparatus of claim 1 wherein each of said coupling tubes is approximately 10 cm long.

15. The apparatus of claim 1 wherein said at least one steel covering comprises woven steel.

16. The apparatus of claim 1 wherein lengths of said coupling tubes are chosen in accordance with a flexural stiffness of said coupling tubes.

17. The apparatus of claim 16 wherein said coupling tubes are sufficiently bendable to allow passage of said apparatus through one or more 1D bends in the pipe or tube.

18. The apparatus of claim 1 wherein the 1D bends comprise 180 degree 1D bends.

* * * * *